(12) United States Patent
Kaufman et al.

(10) Patent No.: US 7,083,783 B2
(45) Date of Patent: Aug. 1, 2006

(54) METHOD FOR TREATING GLAUCOMA

(75) Inventors: Paul L. Kaufman, Madison, WI (US); Xuyang Liu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/060,920

(22) Filed: Feb. 18, 2005

(65) Prior Publication Data

US 2005/0244378 A1 Nov. 3, 2005

Related U.S. Application Data

(60) Provisional application No. 60/545,723, filed on Feb. 18, 2004.

(51) Int. Cl.
*A61K 38/45* (2006.01)
*C12N 9/12* (2006.01)

(52) U.S. Cl. .................. 424/94.5; 435/193; 435/252.3; 435/320.1; 536/23.2

(58) Field of Classification Search ............... 424/94.5; 435/193, 252.3, 320.1; 536/23.2
See application file for complete search history.

(56) References Cited

U.S. PATENT DOCUMENTS

| 5,798,380 | A | 8/1998 | Kaufman et al. |
| 6,110,912 | A | 8/2000 | Kaufman et al. |
| 6,555,107 | B1 | 4/2003 | Poeschla et al. |
| 6,586,425 | B1 | 7/2003 | Kaufman et al. |

OTHER PUBLICATIONS

Andrawiss M., et al., "Adenovirus-mediated gene transfer in canine eyes: a preclinical study for gene therapy of human uveal melanoma," J. Gene. Med., 3:228-239 (2001).
Borras, T., et al., "Ocular adenovirus gene transfer in efficiency and inflammatory response," Invest Ophthalmol. Vis. Sci., 37:1282-1293 (1996).
Borras, T., et al., "Gene transfer to the human trabecular meshwork by anterior segment perfusion," Invest Ophthalmol Vis Sci., 39:1503-1507 (1998).
Borras, T., et al., "Adenoviral reporter gene transfer to the human trabecular meshwork does not alter aqueous humor outflow. Relevance for potential gene therapy of glaucoma," Gene ber 6:515-524 (1999).
Borras, T., et al., "Non-invasive observation of repeated adenoviral GFP gene delivery to the anterior segment of the monkey eye in vivo," J. Gene. Med., 3:437-449 (2001).
Borras, T., et al., "Gene Therapy for Glaucoma: Treating a Multifaceted, Chronic Disease," Invest. Ophthalmol. Vis. Sci., 43:2513 (2002).
Budenz, D., et al., "In vivo gene transfer into murine corneal endothelial and trabecular meshwork cells," Invest. Ophthalmol. Vis. Sci., 36:2211-2215 (1995).
Hauswirth, W. & Beaufrere, L., "Ocular Gene Therapy: Quo Vadis?," Invest. Ophthalmol. Vis. Sci., 41:2821-2826 (2000).
Kee, C., et al., "Stromelysin gene transfer into cultured human trabecular cells and rat trabecular meshwork in vivo," Ophthalmol. Vis. Sci., 42:2856-2860 (2001).
Loewen, N., et al., "Preservation of Aqueous Outflow Facility after Second-Generation FIV Vector-Mediated Expression of Marker Genes in Anterior Segments of Human Eyes," Invest. Ophthalmol. Vis. Sci., 43:3686-3690 (2002).
Loewen, N., et al., "Long-Term, Targeted Genetic Modification of the Aqueous Humor Outflow Tract Coupled with Noninvasive Imaging of Gene Expression In Vivo," Invest. Ophthalmol. Vis. Sci 45:3091-3098 (2004).
Loewen N., et al., "Long-term retinal transgene expression with FIV versus adenoviral vectors," Mol Vis., 10:272-280 (2004).
Nakamura, Y., et al., "Signaling mechanism of TGF-beta 1-induced collagen contraction mediated by bovine trabecular meshworks cells ," Invest. Ophthalmol. Vis. Sci 43:3465-3472 (2002).
Popoff, M., et al., "Characterization of the C3 gene of Clostridium botulinum types C and D and its expression in *Escherichia coli*," Infect. Immun., 59:3673-3679 (1991).

(Continued)

*Primary Examiner*—Tekchand Saidha
(74) *Attorney, Agent, or Firm*—Quarles & Brady LLP

(57) ABSTRACT

A method for increasing outflow facility and reducing intraocular pressure from an eye of a subject having glaucoma includes the step of administering to the eye an amount of an ADP ribosyltransferase protein effective to reduce intraocular pressure and increase outflow facility.

8 Claims, No Drawings

OTHER PUBLICATIONS

Honjo Megumi, et al., "Effects of Rho-associated protein kinase inhibitor Y-27632 on intraocular pressure and outflow facility," IOVS, vol. 42, No. 1, pp. 137-144 (Jan. 2001).

Deng P., et al., "Regulation of trabecular meshwork myosin light chain phosphorylation by Rho/Rho kinase pathway and its influence on aqueous humor outflow facility," Database Biosis Online Biosciences Information Service Philadelphia PA, US (2003).

Wilde C., et al., "the Rho-ADP-ribosylating C3 exoenzyme from Clostridium bofulinum and related C3-like transferases," Toxicon, Elmsford, NY, US, vol. 39, No. 11, pp. 1647-1660 (Nov. 2001).

Rao V., et al., "Rho GTPase inactivation impairs lens growth and integrity," Laboratory Investigation; a Journal of Technical Methods and Pathology, vol. 82, No. 2, pp. 231-239 (Feb. 2002).

EP 1 034 793 A1 (Senju Pharmaceutical Co., Ltd.; Mitsubishi Pharma Corporation) p. 2, paragraph 4-9 (Sep. 13, 2000).

Liu X., et al., "Exoenzyme C3 transferase gene transfer to cultured human trabecular meshwork cells and ciliary muscle cells-towards glaucoma gene therapy," Invest. Ophthalmol. Vis. Scie. Online, vol. 45 (2004).

METHOD FOR TREATING GLAUCOMA

CROSS-REFERENCE TO RELATED APPLICATIONS

This application claims the benefit of U.S. Provisional Patent Application No. 60/545,723, filed Feb. 18, 2004. The provisional application is incorporated by reference in its entirety as if set forth herein.

STATEMENT REGARDING FEDERALLY SPONSORED RESEARCH OR DEVELOPMENT

This invention was made with United States Government Support awarded by the following agency:

NIH, Grant No. EY02698.

The United States Government has certain rights in this invention.

BACKGROUND OF THE INVENTION

The present invention relates to treating ocular disorders and more particularly to treating glaucoma. U.S. Pat. Nos. 5,798,380, 6,110,912, and 6,586,425, each of which is incorporated herein by reference as if set forth in its entirety, describe in detail the nature and etiology of glaucoma and various therapeutic approaches for reducing intraocular pressure characteristic of the disorder. The incorporated patents disclose methods for enhancing aqueous humor outflow and reducing intraocular pressure in the eye of a subject by administering at least one non-corneotoxic ophthalmic preparation which can comprise at least one macrolide. Additional therapeutic modalities employing other agents are still sought.

Exoenzyme C3 transferase (C3) is an ADP ribosyltransferase that inhibits rho-activated cellular contractility, leading to changes in cell shape and to secondary changes in the actin cytoskeleton and cell adhesion. C3 inactivates Rho by selectively ribosylating Rho proteins on asparagine residue 41. While various activities of exoenzyme C3 are known in general, there is no prior indication of advantageous drainage-enhancing and pressure-reducing activities by C3 in animal eyes. A nucleic acid sequence that encodes C3 from *C. botulinum* was disclosed by Popoff, M., et al., "DNA Sequence of Exoenzyme C3, an ADP-ribosyltransferase encoded by *Clostridium botulinum* C and D phages," N. A. R. 18:1291 (1990) (Genbank Accession Number X51464), incorporated by reference as if set forth herein in its entirety. SEQ ID NO:1 presents the nucleic acid sequence that encodes the *C. botulinum* C3 exoenzyme; SEQ ID NO:2 presents the encoded amino acid sequence of the C3 enzyme including a short leader sequence at the N-terminus.

Nakamura, Y. et al., "Signaling Mechanism of TGF-Beta1-Induced Collagen Contraction Mediated by Bovine Trabecular Meshwork Cells," *IOVS*, mention using C3 to prevent the adverse effects of TGF-Beta1 on the pathophysiology of glaucoma, namely matrix contractility. According to Nakamura et al., TGF-Beta1 induces contractility via activation of Rho and the $Ca^{2+}$-dependent enzymes PKC and MLCK and that C3 is one way to inhibit the activity of TGF-Beta1. Nakamura et al. make no suggestion that C3 alone can reduce actomyosin contractility, that it can affect outflow facility, or that C3 would be a useful target for treating glaucoma.

BRIEF SUMMARY OF THE INVENTION

In one aspect, the present invention relates to the observation that overexpression of an ADP ribosyltransferase in cultured human trabecular meshwork cells produces changes in cytoskeleton-cell shape and adhesion changes consistent with changes observed using other agents now known to reduce resistance to fluid drainage and intraocular pressure.

In one embodiment, the present invention describes a method for reducing elevated intraocular pressure or increasing the reduced aqueous humor outflow facility associated with open angle glaucoma in a human or non-human subject having trabecular meshwork cells and having resistance to fluid drainage and intraocular pressure elevated above that considered clinically normal, the method including the step of delivering into the trabecular meshwork cells an ophthalmic preparation that comprises a non-corneotoxic delivery vehicle and a chemical agent, namely an ADP ribosyltransferase protein.

In a related embodiment, the method includes the step of delivering into the trabecular meshwork cells an ophthalmic preparation that comprises an expressible ADP ribosyltransferase-encoding nucleic acid operably linked to a transcriptional promoter active in the trabecular meshwork cells so that expression of the protein in the subject is facilitated after administration.

In either embodiment, the ADP ribosyltransferase protein inhibits Rho-activated cellular contractility, leading to changes in cell shape and to secondary changes in the actin cytoskeleton and cell adhesion. When such changes are induced in the cells of the trabecular meshwork of primate (e.g., monkey or human) eyes by other means, the resistance to fluid drainage, and the intraocular pressure, decrease. Reduced fluid drainage and intraocular pressure elevated to a level capable of causing damage to the optic nerve are characteristic of glaucoma. Reduced contractility and/or perturbation of focal adhesions reduces resistance of the trabecular meshwork to fluid flow and thereby reduces intraocular pressure in a therapeutically useful manner. However, an understanding of the mechanisms (e.g., the specific molecular mechanisms) is not necessary to utilize the present invention. Indeed, it is intended that the present invention not be limited to any particular mechanism(s).

In either embodiment, the ophthalmic preparation can optionally include one or more additional non-corneotoxic agents for reducing intraocular pressure and increasing outflow facility or for such other purpose as may be convenient in a particular case. The delivery vehicle can be conventional, and can include standard salt solutions and preservatives for topical administration, or aqueous or salt solutions without preservatives for intracameral or intracanicular administration.

In certain embodiments, the ADP ribosyltransferase is exoenzyme C3 transferase ("C3").

The technical methods for delivering the protein to the eye, and more particularly to the cells of the trabecular meshwork of the eye, can be conventional and are within the level of skill in the art. In particular embodiments, the administration method is topical delivery to the trabecular meshwork cells. In other embodiments, the administration method is intracameral delivery. In still further embodiments, the route of administration is intracanalicular. In addition, the present invention provides compositions and methods suitable for relaxing actomyosin, the potent contractile machinery that includes actin and myosin filaments.

The present invention provides effective and, in some cases, non-invasive methods for treating glaucoma without causing untoward and unacceptable adverse effects, such as corneal edema.

BRIEF DESCRIPTION OF THE SEVERAL VIEWS OF THE DRAWINGS

Not applicable.

DETAILED DESCRIPTION OF THE INVENTION

The present invention relates to a treatment for glaucoma. While the present invention does not depend on an understanding of the mechanism by which successful treatment is accomplished, it is believed that C3 disrupts the system of focal adhesions and actin and myosin II containing stress fibers, in turn causing changes in cell shape that translate into an increase in aqueous humor outflow facility.

It will be understood, that the use of a genetic construct to provide C3 to an eye of a subject, is considered a desired but not an essential aspect of the administration method. Vectors that are particularly well suited for introduction into non-dividing cells (of which trabecular meshwork cells are an example) are known and are considered desirable for in vivo expression of C3 in vivo in human and non-human animal eyes. A suitable vector can include an adenovirus vector, an adeno-associated virus vector, a herpes simplex virus-based vector, a lentivirus vector, and a plasmid vector. The skilled artisan will appreciate the importance of engineering a vector and its components for efficient use in trabecular meshwork cells. The transduction efficiency of the various delivery systems is known to vary and can depend upon the nature of the vector and its components.

In addition to vectors of the types noted above, non-vector approaches, including direct administration of C3 protein, liposomal delivery of C3, and diffusion of C3 protein from implanted cells encapsulated in a sealed semipermeable membrane capsule, are contemplated.

The use of adenovirus expression vectors and other vector systems for therapeutic transfer of a nucleic acid construct into target tissue to treat glaucoma is described generally in, e.g., Borras, T. et al., "Gene Therapy for Glaucoma: Treating a Multifaceted, Chronic Disease," *IOVS*, 43:2513 (2002) and papers cited therein in references 25–31, each of which is incorporated by reference herein as if set forth in its entirety. Also incorporated herein by reference in its entirety is Hauswirth, W. W. and L. Beaufrere, "Ocular Gene Therapy: Quo Vadis?," *IOVS* 41:2821 (2000) which reviews the eye as a gene therapy target and concludes that "ocular gene therapy seems well poised to be among the earliest successful applications" of the technology. The cited papers also provide the skilled artisan with the technical requirements for a suitable expression vector.

The skilled person will appreciate that when a C3-encoding genetic construct is delivered, various aspects can affect expression of C3 from the encoding construct. For example, the vector backbone of the genetic contruct should be suited for efficient transfer into the target trabecular meshwork cells, for long-term maintenance of the construct in the cells and for sustained expression of C3 in the cells. Expression is sustained, e.g., by providing on the construct a transcriptional promoter that supports transcription in target trabecular meshwork cells. In particular, certain lentivirus vectors, namely certain feline immunodeficiency virus vectors, are efficiently transduced into human and non-human trabecular meshwork cells and provide efficient and long-term stable expression of a protein encoded by a polynucleotide provided on the vector. Suitable vectors, and methods for their production and use, are described in Loewen, N., et al., "Long-Term, Targeted Genetic Modification of the Aqueous Humor Outflow Tract Coupled with Noninvasive Imaging of Gene Expression In Vivo," *IOVS*, 45:3091 (2004) and in Loewen, N., et al., "Preservation of Aqueous Outflow Facility after Second-Generation FIV Vector-Mediated Expression of Marker Genes in Anterior Segments of Human Eyes," *IOVS*, 43:3686 (2002), each of which is incorporated by reference as if set forth herein in its entirety. Further incorporation by reference is made to the papers cited in the foregoing papers in connection with various starting materials and methods for producing vectors suited for efficient transduction into trabecular meshwork cells. Loewen, N., et al. (2004) provides the skilled person with guidance as to the amount of vector advantageously administered in vivo to cats, a species for which effectiveness of a therapeutic method is generally considered to be a reliable predictor of effectiveness of the method in humans. In cats, amounts in the range of between about $10^6$ and $10^8$ tranducing units (TU) were administered per eye with good results. The skilled person applying only routine skill can adjust these amounts, if appropriate, to deliver IOP-reducing amounts of vectors to anterior portions of the eye of human or other non-human subjects. Production of lentiviral vectors and delivery into non-dividing human eye cells is also described and claimed in U.S. Pat. No. 6,555,107, incorporated herein by reference as if set forth in its entirety.

Using conventional tools of the molecular biologist, the aforementioned vectors, and others, can be modified to provide a polynucleotide that encodes C3 in the vector downstream from a transcriptional promoter functional in trabecular meshwork cells, such that C3 is produced in the TM cells.

In the accompanying working examples, C3 was encoded by and expressed from a vector provided with the C3 coding sequences in trabecular meshwork cells grown in culture or maintained in anterior segments mounted on organ perfusion culture dishes. In the examples, C3 and a marker, green fluorescent protein (GFP), were expressed upon introduction into the cells by an adenovirus expression vector under transcriptional control of a cytomegalovirus promoter-enhancer. Introduction by injection of genetic material is considered a preferred approach by the inventors, although provision of C3 protein to trabecular meshwork cells in a manner known to the art is also suitable.

It is also noted that the protein encoded by the C3 coding sequence includes a short (7 amino acid) leader sequence. This sequence is important to the bacterial source, but is not of interest or use in the present invention and can be removed from the coding sequence without adverse effect on intracellular Rho targeting. It is also noted that other ADP-ribosyltransferase exoenzymes, such as the *C. botulinum* C2 toxin, having different targets in the actin microfilament network are known and can be employed in place of exoenzyme C3. However, the C2 enzyme can be more toxic than the C3 enzyme and it would be advantageous to introduce substitution mutations into the enzyme (via the C2-encoding polynucleotide) to modulate the toxicity of C2 before use. A polynucleotide that encodes exoenzyme C2 is available at GenBank accession number D88982 and is attached hereto as SEQ ID NO:3. SEQ ID NO:4 and SEQ ID NO:5 are two components encoded by SEQ ID NO:3. SEQ ID NO:4 has ADP-ribosyltransferase activity.

The skilled artisan will appreciate that in due course further improvements to nucleic acid delivery methods, employing virus- or non-virus based approaches may be developed, and that the invention is sufficiently broad to encompass use of any such methods for providing C3 in trabecular meshwork cells, without regard to the specific delivery vector or method. Further, the C3 protein need not be obtained from *C. botulinum* as in the examples. As the activities of C3 are well understood, the skilled artisan can readily select a C3 protein source having the characteristic properties of C3, namely a ADP ribosyltransferase that inhibits rho-activated cellular contractility, or a nucleic acid sequence encoding same, for administration in the methods of the invention. It will also be understood that the ability of C3 to function in the methods of the invention may be modulated, particularly enhanced, by introducing one or more changes to amino acid residues of the C3 protein. The skilled artisan can introduce such changes at the nucleic acid level and can monitor outflow facility directed by modified proteins such that modified C3 proteins that yield great outflow facility (and nucleic acids encoding same) can be selected for use in the methods. The present invention will be more fully understood upon consideration of the following non-limiting examples. The examples demonstrate proof of principle, but the skilled artisan will appreciate that the C3 can be administered via any medically acceptable route.

In the accompanying working examples, C3 was expressed in trabecular meshwork cells grown in culture. In the examples, C3 and a marker, green fluorescent protein (GFP), were expressed upon introduction into the cells of an adenovirus expression vector under transcriptional control of a cytomegalovirus promoter-enhancer. Introduction by injection of genetic material can increase persistence of the treating agent in the target tissue and is therefore considered a preferred approach by the inventors, although provision of C3 protein to trabecular meshwork cells in a manner known to the art is also suitable. The use of adenovirus expression vectors and other vector systems for therapeutic transfer of a nucleic acid construct into target tissue to treat glaucoma is described generally in, e.g., Borras, T. et al., "Gene Therapy for Glaucoma: Treating a Multifaceted, Chronic Disease," *IOVS*, 43:2513 (2002) and papers cited therein at references 25–31, each of which is incorporated by reference herein as if set forth in its entirety. Also incorporated herein by reference in its entirety is Hauswirth, W. W. and L. Beaufrere, "Ocular Gene Therapy: Quo Vadis?," *IOVS* 41:2821 (2000) which reviews the eye as a gene therapy target and concludes that "ocular gene therapy seems well poised to be among the earliest successful applications" of the technology. The cited papers also provide the skilled artisan with the technical requirements for a suitable expression vector. It will be understood, that the use of a particular adenovirus vector, or an adenovirus vector per se, or, more generally, a genetic construct, to provide C3 to an eye of a subject, is considered a preferred but not an essential administration method. The skilled artisan will appreciate that in due course further improvements to nucleic acid delivery methods, employing virus- or non-virus based approaches will be developed, and that the invention is sufficiently broad to encompass use of any such methods. The present invention will be more fully understood upon consideration of the following non-limiting examples. The examples demonstrate proof of principle, but the skilled artisan will appreciate that the C3 can be administered via any medically acceptable route.

EXAMPLES

Example One

Preparation of Adenovirus Expression Vector Comprising Gene Encoding Exoenzyme C3

A recombinant adenovirus vector that expressed C3 under the control of a human promoter was constructed using the AdEasy XL Adenoviral Vector system (Stratagene, La Jolla). The *C. Botulinum* Exonuclease C3 coding sequences were amplified from a vector containing the C3 gene using forward primer (5' CGG TCG ACA GGC AGG CAT GCA AGC TTA T 3'; SEQ ID NO:6) and reverse primer (5' CGC TCG AGT TTA GGA TTG TAA GCT GTG C 3'; SEQ ID NO:7). The primers used for amplification introduced a SalI restriction enzyme site upstream and a XhoI site downstream of the coding sequence. The amplified SalI-XhoI fragment was cloned into pShuttle-IRES-hrGFP2 (Stratagene). The resulting shuttle vector with insert was co-transfected with pAdEasy (Stratagene) into competent BJ5183 cells under conditions specified by the manufacturer. Recombinant adenovirus clones containing the C3 coding sequence were isolated, then amplified in XL10-Gold® (Stratagene) cells grown in SOC broth (as opposed to NZY+ broth recommended by the system manufacturer). Recombinant adenovirus DNA was linearized and transfected into HEK293 cells, whereupon recombinant adenovirus was packaged. The viral stock was maintained in elution buffer from Puresyn Adenopure purification kit. The titer of adenovirus stock was determined.

Example Two

Use of C3 to Alter Human Trabecular Meshwork (HTM) Cytoskeleton

To determine the effects of adenovirus-mediated C3 gene expression on cultured human trabecular meshwork (HTM) and ciliary muscle (HCM) cells, in vitro studies were performed using HTM and HCM cells infected with the C3-expressing adenovirus vector of Example One and changes in morphology, actin, vinculin and beta-catenin were detected. Cells treated with medium (untreated cells) and virus vector only were used as controls.

Treatment of both HTM and HCM cells with C3-expressing adenovirus resulted in dose-dependent morphological changes 4 days post-infection. C3-treated cells were either partially retracted, rounded up completely or very elongated and attenuated in appearance compared to untreated cells. Compared to virus-treated control cells, which demonstrated prominent stress fibers, C3-treated cells demonstrated either a disrupted or absent actin cytoskeleton. C3-treated cells of both types demonstrated reduced numbers of vinculin-positive focal adhesions compared to controls. In C3-treated HTM cells, vinculin staining at cell-cell junctions was also partially reduced, and there was a near complete loss of beta-catenin staining even in cells that still exhibited an intact actin cytoskeleton, suggesting that cell-cell junctions may be more sensitive to C3 transferase than actin and cell-matrix contacts. Cells treated with the negative control construct did not round up or retract; however some cells appeared somewhat elongated and irregular compared to untreated cells. In conclusion, transduced C3 is effective in disrupting actin and cellular adhesions in HTM and HCM cells.

Example Three (Prophetic)

Use of C3 to Improve Outflow Facility from Organ-Cultured Human and Monkey Anterior Segments Organ cultures of human and monkey eye anterior segments are widely regarded as a preferred system for evaluating and for establishing utility in vivo of proposed human therapeutic modalities. The details of the culture methods and several underlying literature citations are set forth in incorporated U.S. Pat. No. 6,586,425.

The adenoviral vector of Example One can be administered into paired anterior segments of eyes from human or non-human (e.g., rhesus or cynomolgus monkey) animals, the eyes being mounted on organ culture dishes and perfused with DMEM at a constant rate of 2.5 µl/min. For human eyes, following 24 hours of equilibration, baseline OF is calculated as the flow divided by the intraocular pressure (IOP). Human anterior segments are injected with a single dose of $10^7$ pfu of the C3 adenovirus vector to one eye; vehicle to the opposite eye. IOP is monitored continuously for several days and average OF calculated every 6 hours. For monkey segments, baseline OF is determined by two-level constant pressure perfusion for 45–60 min after overnight equilibration. Segments are then injected via the infusion tubing with 80 ul containing $1.5 \times 10^9$ pfu/ml of the control (no C3) vector to one eye; and the C3 vector to the opposite eye. Post-treatment OF is monitored daily beginning two days after injection, continuing for up to 10 days after injection. Human and monkey segments are embedded in optimum cutting temperature cryoembedding matrix (Miles Scientific) and examined for the presence of fluorescence.

Baseline OF (µl/min/mmHg) is similar in the paired eyes. In humans, the IOP begins to decrease in the C3 vector-treated segments after the injection and continues to decrease for the duration of the monitoring. The final OF is increased by at least about 50% in C3-treated segments, while OF of sham-treated segments is substantially unchanged after treatment.

This demonstrates that C3 gene therapy can increase outflow facility in the human and monkey anterior segments in organ culture and has the potential to be used in vivo to control IOP in humans.

Example Four (Prophetic)

Use of C3 to Improve Outflow Facility from Trabecular Meshwork in an Eye of a Living Subject An expressible genetic construct encoding C3 protein is delivered (or C3 protein is administered) to an eye of a human or a non-human subject having reduced outflow facility and elevated intraocular pressure in an amount effective to improve outflow facility and reduce intraocular pressure. Reduced outflow facility and elevated intraocular pressure can be characteristic of glaucoma in a subject. The delivery or administration is achieved in a manner effective to bring C3 protein into contact with the trabecular meshwork of the eye. The amount of material administered in the method can vary depending upon whether the C3 is administered as a protein or as a nucleic acid capable of encoding the C3 protein. In either case, the amount of C3 present in the trabecular meshwork after administration and effective in the method can be in the same order of magnitude as the agents disclosed in incorporated U.S. Pat. No. 6,586,425. Likewise, C3 can be administered in amounts comparable to those administered in the cited patent.

Upon administration, outflow facility is increased and intraocular pressure is reduced relative to pre-administration levels.

Example Five (Prophetic)

Use of C3 to Improve Outflow Facility from Trabecular Meshwork in an Eye of a Living Subject An expressible FIV genetic construct encoding C3 protein is delivered in an amount between about $10^6$ and $10^8$ transducing units to trabecular meshwork cells in an eye of a human or a non-human subject having reduced outflow facility and elevated intraocular pressure. Reduced outflow facility and elevated intraocular pressure can be characteristic of glaucoma in a subject. Upon administration, outflow facility is increased and intraocular pressure is reduced relative to pre-administration levels.

The preceding examples are not intended to limit the scope of the invention, which encompasses all such modifications and variations as fall within the scope of the appended claims.

---

We claim:

1. A method for increasing outflow facility of aqueous humor from an eye having a trabecular meshwork, the method comprising the steps of:
   providing to the trabecular meshwork an amount of an ADP ribosyltransferase protein effective to increase outflow facility.

2. A method as claimed in claim 1 wherein the providing step includes the step of delivering into trabecular meshwork cells a pharmaceutical composition that comprises a non-corneotoxic delivery vehicle and an expression vector that encodes the ADP ribosyltransferase such that ADP ribosyltransferase is produced in an amount effective to increase aqueous humor outflow facility from the trabecular meshwork.

3. A method as claimed in claim 2 wherein the expression vector is selected from the group consisting of an adenovirus vector, an adeno-associated virus vector, a herpes simplex virus-based vector, a lentivirus vector, and a plasmid vector.

4. A method as claimed in claim 2 wherein the expression vector is a lentivirus vector.

5. A method as claimed in claim 1 wherein the ADP ribosyltransferase is exoenzyme C3 transferase.

6. A method as claimed in claim 5 wherein the expression vector is a lentivirus vector.

7. A method as claimed in claim 1 wherein the providing step includes the step of administering a pharmaceutical preparation comprising a non-corneotoxic delivery vehicle and an ADP ribosyltransferase protein to the trabecular meshwork in an amount effective to increase aqueous humor outflow facility from the eye.

8. A method as claimed in claim 7 wherein the ADP ribosyltransferase is exoenzyme C3 transferase.

* * * * *

SEQUENCE LISTING

<160> NUMBER OF SEQ ID NOS: 7

<210> SEQ ID NO 1
<211> LENGTH: 780
<212> TYPE: DNA
<213> ORGANISM: Clostridium botulinum
<220> FEATURE:
<221> NAME/KEY: CDS
<222> LOCATION: (1)..(654)

<400> SEQUENCE: 1

```
gct tat tcc att aat caa aag gct tat tca aat act tac cag gag ttt      48
Ala Tyr Ser Ile Asn Gln Lys Ala Tyr Ser Asn Thr Tyr Gln Glu Phe
1               5                   10                  15 act aat att gat caa gca aaa gct tgg ggt aat gct cag tat aaa aag      96
```

```
                Thr Asn Ile Asp Gln Ala Lys Ala Trp Gly Asn Ala Gln Tyr Lys Lys
                             20                  25                  30 tat gga cta agc aaa tca gaa aaa gaa gct ata gta tca tat act aaa        144
Tyr Gly Leu Ser Lys Ser Glu Lys Glu Ala Ile Val Ser Tyr Thr Lys
             35                  40                  45 agc gct agt gaa ata aat gga aag cta aga caa aat aag gga gtt atc        192
Ser Ala Ser Glu Ile Asn Gly Lys Leu Arg Gln Asn Lys Gly Val Ile
 50                  55                  60 aat gga ttt cct tca aat tta ata aaa caa gtt gaa ctt tta gat aaa        240
Asn Gly Phe Pro Ser Asn Leu Ile Lys Gln Val Glu Leu Leu Asp Lys
 65                  70                  75                  80 tct ttt aat aaa atg aag acc cct gaa aat att atg tta ttt aga ggc        288
Ser Phe Asn Lys Met Lys Thr Pro Glu Asn Ile Met Leu Phe Arg Gly
                 85                  90                  95 gac gac cct gct tat tta gga aca gaa ttt caa aac act ctt ctt aat        336
Asp Asp Pro Ala Tyr Leu Gly Thr Glu Phe Gln Asn Thr Leu Leu Asn
             100                 105                 110 tca aat ggt aca att aat aaa acg gct ttt gaa aag gct aaa gct aag        384
Ser Asn Gly Thr Ile Asn Lys Thr Ala Phe Glu Lys Ala Lys Ala Lys
         115                 120                 125 ttt tta aat aaa gat aga ctt gaa tat gga tat att agt act tca tta        432
Phe Leu Asn Lys Asp Arg Leu Glu Tyr Gly Tyr Ile Ser Thr Ser Leu
130                 135                 140 atg aat gtt tct caa ttt gca gga aga cca att att aca aaa ttt aaa        480
Met Asn Val Ser Gln Phe Ala Gly Arg Pro Ile Ile Thr Lys Phe Lys
145                 150                 155                 160 gta gca aaa ggc tca aag gca gga tat att gac cct att agt gct ttt        528
Val Ala Lys Gly Ser Lys Ala Gly Tyr Ile Asp Pro Ile Ser Ala Phe
                 165                 170                 175 gca gga caa ctt gaa atg ttg ctt cct aga cat agt act tat cat ata        576
Ala Gly Gln Leu Glu Met Leu Leu Pro Arg His Ser Thr Tyr His Ile
             180                 185                 190 gac gat atg aga ttg tct tct gat ggt aaa caa ata ata att aca gca        624
Asp Asp Met Arg Leu Ser Ser Asp Gly Lys Gln Ile Ile Ile Thr Ala
         195                 200                 205 aca atg atg ggc aca gct atc aat cct aaa taatagagct attagcatgt         674
Thr Met Met Gly Thr Ala Ile Asn Pro Lys
     210                 215 taaggaattg tatataatta aatgtaaaaa gagttacttt ataacaaagt agctcttttt     734
actataagca aaaataagac tgctatttat acccaatata tggcaa                   780

<210> SEQ ID NO 2
<211> LENGTH: 218
<212> TYPE: PRT
<213> ORGANISM: Clostridium botulinum

<400> SEQUENCE: 2

Ala Tyr Ser Ile Asn Gln Lys Ala Tyr Ser Asn Thr Tyr Gln Glu Phe
1               5                   10                  15

Thr Asn Ile Asp Gln Ala Lys Ala Trp Gly Asn Ala Gln Tyr Lys Lys
             20                  25                  30

Tyr Gly Leu Ser Lys Ser Glu Lys Glu Ala Ile Val Ser Tyr Thr Lys
         35                  40                  45

Ser Ala Ser Glu Ile Asn Gly Lys Leu Arg Gln Asn Lys Gly Val Ile
     50                  55                  60

Asn Gly Phe Pro Ser Asn Leu Ile Lys Gln Val Glu Leu Leu Asp Lys
65                  70                  75                  80

Ser Phe Asn Lys Met Lys Thr Pro Glu Asn Ile Met Leu Phe Arg Gly
```

-continued

```
                        85                  90                  95
Asp Asp Pro Ala Tyr Leu Gly Thr Glu Phe Gln Asn Thr Leu Leu Asn
            100                 105                 110
Ser Asn Gly Thr Ile Asn Lys Thr Ala Phe Glu Lys Ala Lys Ala Lys
            115                 120                 125
Phe Leu Asn Lys Asp Arg Leu Glu Tyr Gly Tyr Ile Ser Thr Ser Leu
            130                 135                 140
Met Asn Val Ser Gln Phe Ala Gly Arg Pro Ile Ile Thr Lys Phe Lys
145                 150                 155                 160
Val Ala Lys Gly Ser Lys Ala Gly Tyr Ile Asp Pro Ile Ser Ala Phe
                165                 170                 175
Ala Gly Gln Leu Glu Met Leu Leu Pro Arg His Ser Thr Tyr His Ile
            180                 185                 190
Asp Asp Met Arg Leu Ser Ser Asp Gly Lys Gln Ile Ile Ile Thr Ala
            195                 200                 205
Thr Met Met Gly Thr Ala Ile Asn Pro Lys
            210                 215

<210> SEQ ID NO 3
<211> LENGTH: 4557
<212> TYPE: DNA
<213> ORGANISM: Clostridium botulinum
<220> FEATURE:
<221> NAME/KEY: CDS
<222> LOCATION: (154)..(1449)
<223> OTHER INFORMATION: Feature encodes Component 1 (ADP
      ribosyltransferase)
<220> FEATURE:
<221> NAME/KEY: CDS
<222> LOCATION: (1696)..(3861)

<400> SEQUENCE: 3
caacaaaaaa ttatagtata aattctattg catgtacata ataactttt atatagctta      60 aaatgtatca aaatagaatt aacttgaata caatataatg cactatattg tcgtataatg    120
cattatatta tcataacaag gggagaatta tat atg cca ata ata aaa gaa ccc    174
                                    Met Pro Ile Ile Lys Glu Pro
                                    1               5 att gac ttt atc aat aaa cct gaa tct gaa gcc caa aaa tgg ggc aaa     222
Ile Asp Phe Ile Asn Lys Pro Glu Ser Glu Ala Gln Lys Trp Gly Lys
        10                  15                  20 gaa gaa gaa aaa cgt tgg ttt acg aaa tta aat aat ctt gaa gaa gta     270
Glu Glu Glu Lys Arg Trp Phe Thr Lys Leu Asn Asn Leu Glu Glu Val
    25                  30                  35 gcc gta aat caa ctt aaa act aag gaa gat aaa aca aaa ata gat aat     318
Ala Val Asn Gln Leu Lys Thr Lys Glu Asp Lys Thr Lys Ile Asp Asn
40                  45                  50                  55 ttt tct aca gac att tta ttt tct tca tta act gca ata gaa att atg     366
Phe Ser Thr Asp Ile Leu Phe Ser Ser Leu Thr Ala Ile Glu Ile Met
                60                  65                  70 aaa gaa gac gaa aat caa aat ctt ttt gat gtt gaa aga att aga gaa     414
Lys Glu Asp Glu Asn Gln Asn Leu Phe Asp Val Glu Arg Ile Arg Glu
            75                  80                  85 gca ctt tta aaa aat act tta gat aga gaa gtt ata ggc tat gta aat     462
Ala Leu Leu Lys Asn Thr Leu Asp Arg Glu Val Ile Gly Tyr Val Asn
        90                  95                  100 ttt aca cct aaa gag ctt gga att aat ttt tct ata aga gat gta gaa     510
Phe Thr Pro Lys Glu Leu Gly Ile Asn Phe Ser Ile Arg Asp Val Glu
    105                 110                 115 tta aat aga gat ata tca gat gaa att tta gat aaa gtt aga cag caa     558
```

| | | |
|---|---|---|
| Leu Asn Arg Asp Ile Ser Asp Glu Ile Leu Asp Lys Val Arg Gln Gln<br>120                       125                  130                     135 | |
| ata ata aat caa gaa tat act aaa ttt tca ttt gta tca tta ggg tta<br>Ile Ile Asn Gln Glu Tyr Thr Lys Phe Ser Phe Val Ser Leu Gly Leu<br>                    140                  145                  150 | 606 |
| aat gac aac agc atc gat gag agt ata cca gtt att gtg aaa act aga<br>Asn Asp Asn Ser Ile Asp Glu Ser Ile Pro Val Ile Val Lys Thr Arg<br>                155                  160                  165 | 654 |
| gtt cca aca acg ttt aat tat ggt gtt ctt aat aat aaa gaa aca gta<br>Val Pro Thr Thr Phe Asn Tyr Gly Val Leu Asn Asn Lys Glu Thr Val<br>        170                  175                  180 | 702 |
| tca tta tta tta aat caa ggt ttt tct ata att cct gag tca gct att<br>Ser Leu Leu Leu Asn Gln Gly Phe Ser Ile Ile Pro Glu Ser Ala Ile<br>      185                  190                  195 | 750 |
| ata act act ata aaa gga aaa gac tat ata tta ata gaa gga agt ctt<br>Ile Thr Thr Ile Lys Gly Lys Asp Tyr Ile Leu Ile Glu Gly Ser Leu<br>200                       205                  210                  215 | 798 |
| agt caa gag ctt gat ttc tat aat aaa gga tca gaa gct tgg gga gaa<br>Ser Gln Glu Leu Asp Phe Tyr Asn Lys Gly Ser Glu Ala Trp Gly Glu<br>                220                  225                  230 | 846 |
| aaa aat tat ggt gat tat gtt tca aaa ctt tcc cag gaa caa tta ggt<br>Lys Asn Tyr Gly Asp Tyr Val Ser Lys Leu Ser Gln Glu Gln Leu Gly<br>        235                  240                  245 | 894 |
| gct tta gaa gga tat ctg cat tca gat tat aaa gct att aat agt tat<br>Ala Leu Glu Gly Tyr Leu His Ser Asp Tyr Lys Ala Ile Asn Ser Tyr<br>      250                  255                  260 | 942 |
| tta aga aat aat aga gtt cca aat aat gac gag ctt aat aaa aaa att<br>Leu Arg Asn Asn Arg Val Pro Asn Asn Asp Glu Leu Asn Lys Lys Ile<br>265                       270                  275 | 990 |
| gaa tta ata agt tct gct cta tct gta aag cca ata ccc gaa aca tta<br>Glu Leu Ile Ser Ser Ala Leu Ser Val Lys Pro Ile Pro Glu Thr Leu<br>280                       285                  290                  295 | 1038 |
| ata gca tat aga aga gta gat ggt att cca ttc gat tta cct tct gat<br>Ile Ala Tyr Arg Arg Val Asp Gly Ile Pro Phe Asp Leu Pro Ser Asp<br>                300                  305                  310 | 1086 |
| ttt tcc ttt gat aaa aaa gaa aat ggt gaa ata ata gct gat aaa aca<br>Phe Ser Phe Asp Lys Lys Glu Asn Gly Glu Ile Ile Ala Asp Lys Thr<br>        315                  320                  325 | 1134 |
| aaa tta aac gag ttt ata gat aaa tgg act gga aaa gaa att gaa aat<br>Lys Leu Asn Glu Phe Ile Asp Lys Trp Thr Gly Lys Glu Ile Glu Asn<br>      330                  335                  340 | 1182 |
| tta tca ttt tct agt act tct ctt aaa tcc acc cca tta tca ttt agt<br>Leu Ser Phe Ser Ser Thr Ser Leu Lys Ser Thr Pro Leu Ser Phe Ser<br>345                       350                  355 | 1230 |
| aaa tct cgt ttt ata ttt aga ttg cgt tta agt gaa ggg acc att gga<br>Lys Ser Arg Phe Ile Phe Arg Leu Arg Leu Ser Glu Gly Thr Ile Gly<br>360                       365                  370                  375 | 1278 |
| gcg ttt att tat ggg ttt tct gga ttt caa gat gaa caa gaa att ctt<br>Ala Phe Ile Tyr Gly Phe Ser Gly Phe Gln Asp Glu Gln Glu Ile Leu<br>                380                  385                  390 | 1326 |
| tta aat aag aat tct act ttc aag ata ttt aga ata act cca ata act<br>Leu Asn Lys Asn Ser Thr Phe Lys Ile Phe Arg Ile Thr Pro Ile Thr<br>        395                  400                  405 | 1374 |
| tca ata att aat aga gtt act aaa atg act cag gta gta att gat gct<br>Ser Ile Ile Asn Arg Val Thr Lys Met Thr Gln Val Val Ile Asp Ala<br>      410                  415                  420 | 1422 |
| gaa gtt ata caa aat aaa gag att tag catcaataaa taatattcct<br>Glu Val Ile Gln Asn Lys Glu Ile<br>425                     430 | 1469 |

-continued

```
attgaaataa gattctaagg acaatactct aaacttttaa ataaaagatt tgtagtattg   1529
tcctttaatt atattttctc gaattctaca tttttcgtca catttttta ttagatttca    1589 taaaatatta aagtacacta atgttttatg aaaaagtgta ctaactgatg ataagaatta   1649
taagtaaaca ataatattct aaagataaaa ttaggagagt gcattt atg tta gtt      1704
                                                   Met Leu Val tca aaa ttt gag aac tct gta aaa aat tca aat aaa aat tat ttc aca     1752
Ser Lys Phe Glu Asn Ser Val Lys Asn Ser Asn Lys Asn Tyr Phe Thr
435             440             445             450 ata aac ggt tta atg ggg tat tat ttt gaa aat gat ttt ttt aat tta     1800
Ile Asn Gly Leu Met Gly Tyr Tyr Phe Glu Asn Asp Phe Phe Asn Leu
                455             460             465 aat ata ata tca cca act tta gat gga aat tta act ttt agt aaa gag     1848
Asn Ile Ile Ser Pro Thr Leu Asp Gly Asn Leu Thr Phe Ser Lys Glu
            470             475             480 gat att aat tca atc tta ggt aat aaa atc att aag tct gca aga tgg     1896
Asp Ile Asn Ser Ile Leu Gly Asn Lys Ile Ile Lys Ser Ala Arg Trp
                485             490             495 att ggc tta ata aag cct agt ata act gga gaa tat att tta tca aca     1944
Ile Gly Leu Ile Lys Pro Ser Ile Thr Gly Glu Tyr Ile Leu Ser Thr
500             505             510 aat agt cct aat tgt aga gtt gaa cta aat ggt gaa ata ttt aac cta     1992
Asn Ser Pro Asn Cys Arg Val Glu Leu Asn Gly Glu Ile Phe Asn Leu
515             520             525             530 tct tta aac aca tct aat act gtt aat tta att caa gga aac gtt tat     2040
Ser Leu Asn Thr Ser Asn Thr Val Asn Leu Ile Gln Gly Asn Val Tyr
                535             540             545 gac atc aga ata gaa caa tta atg tca gaa aat cag tta tta aaa aat     2088
Asp Ile Arg Ile Glu Gln Leu Met Ser Glu Asn Gln Leu Leu Lys Asn
                550             555             560 tat gaa gga att aag ctt tac tgg gaa act tcg gat att ata aaa gaa     2136
Tyr Glu Gly Ile Lys Leu Tyr Trp Glu Thr Ser Asp Ile Ile Lys Glu
                565             570             575 ata att cct tca gaa gta ttg tta aaa ccc aat tat agt aat aca aat     2184
Ile Ile Pro Ser Glu Val Leu Leu Lys Pro Asn Tyr Ser Asn Thr Asn
580             585             590 gag aaa tct aaa ttt att cct aat aat aca ctg ttc tct aat gct aaa     2232
Glu Lys Ser Lys Phe Ile Pro Asn Asn Thr Leu Phe Ser Asn Ala Lys
595             600             605             610 tta aag gct aat gca aat aga gat act gat aga gat ggt ata cct gat     2280
Leu Lys Ala Asn Ala Asn Arg Asp Thr Asp Arg Asp Gly Ile Pro Asp
                615             620             625 gaa tgg gaa att aat gga tat acg gtt atg aat caa aaa gct gta gca     2328
Glu Trp Glu Ile Asn Gly Tyr Thr Val Met Asn Gln Lys Ala Val Ala
                630             635             640 tgg gat gat aaa ttt gca gct aat ggt tat aaa aaa tat gta tct aat     2376
Trp Asp Asp Lys Phe Ala Ala Asn Gly Tyr Lys Lys Tyr Val Ser Asn
                645             650             655 cct ttt aaa cct tgt act gca aat gac cca tat aca gac ttt gaa aaa     2424
Pro Phe Lys Pro Cys Thr Ala Asn Asp Pro Tyr Thr Asp Phe Glu Lys
660             665             670 gtt tca gga caa ata gat cca tct gta agt atg gta gca aga gat cca     2472
Val Ser Gly Gln Ile Asp Pro Ser Val Ser Met Val Ala Arg Asp Pro
675             680             685             690 atg ata tct gct tat cct ata gtt gga gtc caa atg gaa aga tta gtt     2520
Met Ile Ser Ala Tyr Pro Ile Val Gly Val Gln Met Glu Arg Leu Val
                695             700             705 gtt tct aaa tca gaa aca att act gga gat tca act aag agt atg tct     2568
Val Ser Lys Ser Glu Thr Ile Thr Gly Asp Ser Thr Lys Ser Met Ser
```

-continued

```
                 710                 715                 720
aaa tca act agt cat agt agt act aat att aat act gtt ggc gca gaa    2616
Lys Ser Thr Ser His Ser Ser Thr Asn Ile Asn Thr Val Gly Ala Glu
        725                 730                 735 gtt tca ggt agt tta caa ctt gct gga ggt ata ttc cct gta ttt agc    2664
Val Ser Gly Ser Leu Gln Leu Ala Gly Gly Ile Phe Pro Val Phe Ser
    740                 745                 750 atg tct gct tca gca aat tat tct cac aca tgg caa aat aca agt aca    2712
Met Ser Ala Ser Ala Asn Tyr Ser His Thr Trp Gln Asn Thr Ser Thr
755                 760                 765                 770 gtt gat gat aca act gga gaa agt ttc tct caa gga tta agt ata aat    2760
Val Asp Asp Thr Thr Gly Glu Ser Phe Ser Gln Gly Leu Ser Ile Asn
                775                 780                 785 act ggt gaa tcc gct tat ata aat cct aat att aga tat tat aat act    2808
Thr Gly Glu Ser Ala Tyr Ile Asn Pro Asn Ile Arg Tyr Tyr Asn Thr
            790                 795                 800 ggt act gct cca gtg tat aat gtt act ccc act act acc ata gta att    2856
Gly Thr Ala Pro Val Tyr Asn Val Thr Pro Thr Thr Thr Ile Val Ile
        805                 810                 815 gat aaa caa tct gta gcc act att aag gga caa gaa agc tta att ggg    2904
Asp Lys Gln Ser Val Ala Thr Ile Lys Gly Gln Glu Ser Leu Ile Gly
    820                 825                 830 gac tat cta aat cct ggt gga acc tat cct att ata gga gaa cct cct    2952
Asp Tyr Leu Asn Pro Gly Gly Thr Tyr Pro Ile Ile Gly Glu Pro Pro
835                 840                 845                 850 atg gct tta aat act atg gat caa ttt agt agt cgt tta att ccg ata    3000
Met Ala Leu Asn Thr Met Asp Gln Phe Ser Ser Arg Leu Ile Pro Ile
                855                 860                 865 aat tac aat caa tta aaa agc att gat aat ggt gga act gta atg tta    3048
Asn Tyr Asn Gln Leu Lys Ser Ile Asp Asn Gly Gly Thr Val Met Leu
            870                 875                 880 tcg aca tcc cag ttt act gga aac ttt gcc aaa tat aat tcc aac ggt    3096
Ser Thr Ser Gln Phe Thr Gly Asn Phe Ala Lys Tyr Asn Ser Asn Gly
        885                 890                 895 aat tta gta act gat gga aac aat tgg gga cct tat tta ggt act ata    3144
Asn Leu Val Thr Asp Gly Asn Asn Trp Gly Pro Tyr Leu Gly Thr Ile
    900                 905                 910 aaa agt aca aca gct tca tta act tta tct ttc tct ggt caa act act    3192
Lys Ser Thr Thr Ala Ser Leu Thr Leu Ser Phe Ser Gly Gln Thr Thr
915                 920                 925                 930 caa gtt gct gtt gtt gct cct aat ttt agt gat cct gaa gat aaa act    3240
Gln Val Ala Val Val Ala Pro Asn Phe Ser Asp Pro Glu Asp Lys Thr
                935                 940                 945 cct aaa tta act ttg gaa caa gct cta gtt aaa gct ttc gca ctt gaa    3288
Pro Lys Leu Thr Leu Glu Gln Ala Leu Val Lys Ala Phe Ala Leu Glu
            950                 955                 960 aag aaa aat ggt aaa ttt tat ttt cat ggt tta gaa att agt aaa aat    3336
Lys Lys Asn Gly Lys Phe Tyr Phe His Gly Leu Glu Ile Ser Lys Asn
        965                 970                 975 gaa aaa ata caa gta ttt tta gat agt aat aca aat aat gat ttt gaa    3384
Glu Lys Ile Gln Val Phe Leu Asp Ser Asn Thr Asn Asn Asp Phe Glu
    980                 985                 990 aat caa tta aaa aat aca  gct gat aaa gat att  atg cat tgt ata     3429
Asn Gln Leu Lys Asn Thr  Ala Asp Lys Asp Ile  Met His Cys Ile
995                 1000                 1005 ata  aaa cgt aat atg aat  att tta gta aaa gta  att act ttt aaa    3474
Ile  Lys Arg Asn Met Asn  Ile Leu Val Lys Val  Ile Thr Phe Lys
1010                 1015                 1020 gaa  aat ata tcc tca atc  aat atc ata aat gat  act aat ttt ggt    3519
```

```
Glu Asn Ile Ser Ser Ile Asn Ile Ile Asn Asp Thr Asn Phe Gly
1025                1030                1035 gtt caa tct atg aca ggt ctt tct aat aga tct aaa gga caa gat         3564
Val Gln Ser Met Thr Gly Leu Ser Asn Arg Ser Lys Gly Gln Asp
1040                1045                1050 ggt atc tat aga gct gct aca aca gct ttt tct ttt aaa tct aaa         3609
Gly Ile Tyr Arg Ala Ala Thr Thr Ala Phe Ser Phe Lys Ser Lys
1055                1060                1065 gaa cta aaa tat cca gaa ggt cgt tat aga atg cgt ttt gta att         3654
Glu Leu Lys Tyr Pro Glu Gly Arg Tyr Arg Met Arg Phe Val Ile
1070                1075                1080 caa tct tat gaa ccg ttt acc tgt aac ttt aaa ctc ttt aat aac         3699
Gln Ser Tyr Glu Pro Phe Thr Cys Asn Phe Lys Leu Phe Asn Asn
1085                1090                1095 cta ata tat tct agt tca ttt gat aaa gga tat tat gat gaa ttt         3744
Leu Ile Tyr Ser Ser Ser Phe Asp Lys Gly Tyr Tyr Asp Glu Phe
1100                1105                1110 ttt tac ttt tat tat aat ggc agt aaa tct ttt ttt aat att tct         3789
Phe Tyr Phe Tyr Tyr Asn Gly Ser Lys Ser Phe Phe Asn Ile Ser
1115                1120                1125 tgt gat att ata aat tct att aat agg ctt tcg ggg gtt ttc tta         3834
Cys Asp Ile Ile Asn Ser Ile Asn Arg Leu Ser Gly Val Phe Leu
1130                1135                1140 ata gaa tta gat aaa tta ata ata tag tatctataaa aattatgaat           3881
Ile Glu Leu Asp Lys Leu Ile Ile
1145                1150 aacaccaatt cgggtcatgt attattaaag actacgagta agatttaaat taaaatgtat   3941
cctatgaagt agacgattta aaaaagctta cttcataggg tatttttatg tataatagaa   4001
taaagaaaat ttaagatgct ttagatacta gggatatagt agcataatag tgagttgtat   4061
actgtaaggt ttaatacaga tggttttagt aattataaac tagatagtaa attacattca   4121
aaaataatag aaaaggatga agttaaaat gaaaatagg attagtttt gaaataaaat      4181 attagggca atacttatat tagttggtat tataccctata tatttaattt tatgtatata   4241
tccatttaaa ggatttaatt cttttataga atctctaaaa tgggcattta cagaaagctg   4301
cgataaggat ttgcatataa ttggaactat gtgtttttt actggtttaa taataataat   4361
aaatgacagg ataaaaaata acaaaattaa aaaatagtta atatttttta taatggaaaa   4421
tgtggatgta atagttttat tttattttca aattcatgtg taactttagt tttaccaata   4481
acataaacat tattatcata attaggattt ataagcgg attcaccagt atttatactt    4541
aatccttgag agaaac                                                   4557

<210> SEQ ID NO 4
<211> LENGTH: 431
<212> TYPE: PRT
<213> ORGANISM: Clostridium botulinum

<400> SEQUENCE: 4

Met Pro Ile Ile Lys Glu Pro Ile Asp Phe Ile Asn Lys Pro Glu Ser
1               5                   10                  15

Glu Ala Gln Lys Trp Gly Lys Glu Glu Lys Arg Trp Phe Thr Lys
                20                  25                  30

Leu Asn Asn Leu Glu Glu Val Ala Val Asn Gln Leu Lys Thr Lys Glu
                35                  40                  45

Asp Lys Thr Lys Ile Asp Asn Phe Ser Thr Asp Ile Leu Phe Ser Ser
50                  55                  60
```

-continued

```
Leu Thr Ala Ile Glu Ile Met Lys Glu Asp Glu Asn Gln Asn Leu Phe
 65                  70                  75                  80

Asp Val Glu Arg Ile Arg Glu Ala Leu Leu Lys Asn Thr Leu Asp Arg
                 85                  90                  95

Glu Val Ile Gly Tyr Val Asn Phe Thr Pro Lys Glu Leu Gly Ile Asn
            100                 105                 110

Phe Ser Ile Arg Asp Val Glu Leu Asn Arg Asp Ile Ser Asp Glu Ile
        115                 120                 125

Leu Asp Lys Val Arg Gln Gln Ile Ile Asn Gln Glu Tyr Thr Lys Phe
    130                 135                 140

Ser Phe Val Ser Leu Gly Leu Asn Asp Asn Ser Ile Asp Glu Ser Ile
145                 150                 155                 160

Pro Val Ile Val Lys Thr Arg Val Pro Thr Thr Phe Asn Tyr Gly Val
                165                 170                 175

Leu Asn Asn Lys Glu Thr Val Ser Leu Leu Asn Gln Gly Phe Ser
                180                 185                 190

Ile Ile Pro Glu Ser Ala Ile Ile Thr Thr Ile Lys Gly Lys Asp Tyr
        195                 200                 205

Ile Leu Ile Glu Gly Ser Leu Ser Gln Glu Leu Asp Phe Tyr Asn Lys
    210                 215                 220

Gly Ser Glu Ala Trp Gly Glu Lys Asn Tyr Gly Asp Tyr Val Ser Lys
225                 230                 235                 240

Leu Ser Gln Glu Gln Leu Gly Ala Leu Glu Gly Tyr Leu His Ser Asp
                245                 250                 255

Tyr Lys Ala Ile Asn Ser Tyr Leu Arg Asn Asn Arg Val Pro Asn Asn
            260                 265                 270

Asp Glu Leu Asn Lys Lys Ile Glu Leu Ile Ser Ser Ala Leu Ser Val
        275                 280                 285

Lys Pro Ile Pro Glu Thr Leu Ile Ala Tyr Arg Arg Val Asp Gly Ile
    290                 295                 300

Pro Phe Asp Leu Pro Ser Asp Phe Ser Phe Asp Lys Lys Glu Asn Gly
305                 310                 315                 320

Glu Ile Ile Ala Asp Lys Thr Lys Leu Asn Glu Phe Ile Asp Lys Trp
                325                 330                 335

Thr Gly Lys Glu Ile Glu Asn Leu Ser Phe Ser Ser Thr Ser Leu Lys
            340                 345                 350

Ser Thr Pro Leu Ser Phe Ser Lys Ser Arg Phe Ile Phe Arg Leu Arg
        355                 360                 365

Leu Ser Glu Gly Thr Ile Gly Ala Phe Ile Tyr Gly Phe Ser Gly Phe
    370                 375                 380

Gln Asp Glu Gln Glu Ile Leu Leu Asn Lys Asn Ser Thr Phe Lys Ile
385                 390                 395                 400

Phe Arg Ile Thr Pro Ile Thr Ser Ile Ile Asn Arg Val Thr Lys Met
                405                 410                 415

Thr Gln Val Val Ile Asp Ala Glu Val Ile Gln Asn Lys Glu Ile
            420                 425                 430
```

<210> SEQ ID NO 5
<211> LENGTH: 721
<212> TYPE: PRT
<213> ORGANISM: Clostridium botulinum

<400> SEQUENCE: 5

```
Met Leu Val Ser Lys Phe Glu Asn Ser Val Lys Asn Ser Asn Lys Asn
  1               5                  10                  15
```

-continued

```
Tyr Phe Thr Ile Asn Gly Leu Met Gly Tyr Tyr Phe Glu Asn Asp Phe
            20                  25                  30

Phe Asn Leu Asn Ile Ile Ser Pro Thr Leu Asp Gly Asn Leu Thr Phe
            35                  40                  45

Ser Lys Glu Asp Ile Asn Ser Ile Leu Gly Asn Lys Ile Ile Lys Ser
    50                  55                  60

Ala Arg Trp Ile Gly Leu Ile Lys Pro Ser Ile Thr Gly Glu Tyr Ile
65                  70                  75                  80

Leu Ser Thr Asn Ser Pro Asn Cys Arg Val Glu Leu Asn Gly Glu Ile
                85                  90                  95

Phe Asn Leu Ser Leu Asn Thr Ser Asn Thr Val Asn Leu Ile Gln Gly
            100                 105                 110

Asn Val Tyr Asp Ile Arg Ile Glu Gln Leu Met Ser Glu Asn Gln Leu
            115                 120                 125

Leu Lys Asn Tyr Glu Gly Ile Lys Leu Tyr Trp Glu Thr Ser Asp Ile
    130                 135                 140

Ile Lys Glu Ile Ile Pro Ser Glu Val Leu Leu Lys Pro Asn Tyr Ser
145                 150                 155                 160

Asn Thr Asn Glu Lys Ser Lys Phe Ile Pro Asn Asn Thr Leu Phe Ser
                165                 170                 175

Asn Ala Lys Leu Lys Ala Asn Ala Asn Arg Asp Thr Asp Arg Asp Gly
            180                 185                 190

Ile Pro Asp Glu Trp Glu Ile Asn Gly Tyr Thr Val Met Asn Gln Lys
            195                 200                 205

Ala Val Ala Trp Asp Asp Lys Phe Ala Ala Asn Gly Tyr Lys Lys Tyr
    210                 215                 220

Val Ser Asn Pro Phe Lys Pro Cys Thr Ala Asn Asp Pro Tyr Thr Asp
225                 230                 235                 240

Phe Glu Lys Val Ser Gly Gln Ile Asp Pro Ser Val Ser Met Val Ala
                245                 250                 255

Arg Asp Pro Met Ile Ser Ala Tyr Pro Ile Val Gly Val Gln Met Glu
            260                 265                 270

Arg Leu Val Val Ser Lys Ser Glu Thr Ile Thr Gly Asp Ser Thr Lys
            275                 280                 285

Ser Met Ser Lys Ser Thr Ser His Ser Ser Thr Asn Ile Asn Thr Val
    290                 295                 300

Gly Ala Glu Val Ser Gly Ser Leu Gln Leu Ala Gly Gly Ile Phe Pro
305                 310                 315                 320

Val Phe Ser Met Ser Ala Ser Ala Asn Tyr Ser His Thr Trp Gln Asn
                325                 330                 335

Thr Ser Thr Val Asp Asp Thr Thr Gly Glu Ser Phe Ser Gln Gly Leu
            340                 345                 350

Ser Ile Asn Thr Gly Glu Ser Ala Tyr Ile Asn Pro Asn Ile Arg Tyr
            355                 360                 365

Tyr Asn Thr Gly Thr Ala Pro Val Tyr Asn Val Thr Pro Thr Thr Thr
    370                 375                 380

Ile Val Ile Asp Lys Gln Ser Val Ala Thr Ile Lys Gly Gln Glu Ser
385                 390                 395                 400

Leu Ile Gly Asp Tyr Leu Asn Pro Gly Gly Thr Tyr Pro Ile Ile Gly
                405                 410                 415

Glu Pro Pro Met Ala Leu Asn Thr Met Asp Gln Phe Ser Ser Arg Leu
            420                 425                 430
```

```
Ile Pro Ile Asn Tyr Asn Gln Leu Lys Ser Ile Asp Asn Gly Gly Thr
            435                 440                 445
Val Met Leu Ser Thr Ser Gln Phe Thr Gly Asn Phe Ala Lys Tyr Asn
            450                 455                 460
Ser Asn Gly Asn Leu Val Thr Asp Gly Asn Asn Trp Gly Pro Tyr Leu
465                 470                 475                 480
Gly Thr Ile Lys Ser Thr Thr Ala Ser Leu Thr Leu Ser Phe Ser Gly
                    485                 490                 495
Gln Thr Thr Gln Val Ala Val Ala Pro Asn Phe Ser Asp Pro Glu
            500                 505                 510
Asp Lys Thr Pro Lys Leu Thr Leu Glu Gln Ala Leu Val Lys Ala Phe
            515                 520                 525
Ala Leu Glu Lys Lys Asn Gly Lys Phe Tyr Phe His Gly Leu Glu Ile
            530                 535                 540
Ser Lys Asn Glu Lys Ile Gln Val Phe Leu Asp Ser Asn Thr Asn Asn
545                 550                 555                 560
Asp Phe Glu Asn Gln Leu Lys Asn Thr Ala Asp Lys Asp Ile Met His
                    565                 570                 575
Cys Ile Ile Lys Arg Asn Met Asn Ile Leu Val Lys Val Ile Thr Phe
            580                 585                 590
Lys Glu Asn Ile Ser Ser Ile Asn Ile Ile Asn Asp Thr Asn Phe Gly
            595                 600                 605
Val Gln Ser Met Thr Gly Leu Ser Asn Arg Ser Lys Gly Gln Asp Gly
            610                 615                 620
Ile Tyr Arg Ala Ala Thr Thr Ala Phe Ser Phe Lys Ser Lys Glu Leu
625                 630                 635                 640
Lys Tyr Pro Glu Gly Arg Tyr Arg Met Arg Phe Val Ile Gln Ser Tyr
                    645                 650                 655
Glu Pro Phe Thr Cys Asn Phe Lys Leu Phe Asn Asn Leu Ile Tyr Ser
                660                 665                 670
Ser Ser Phe Asp Lys Gly Tyr Tyr Asp Glu Phe Phe Tyr Phe Tyr Tyr
            675                 680                 685
Asn Gly Ser Lys Ser Phe Phe Asn Ile Ser Cys Asp Ile Ile Asn Ser
            690                 695                 700
Ile Asn Arg Leu Ser Gly Val Phe Leu Ile Glu Leu Asp Lys Leu Ile
705                 710                 715                 720
Ile

<210> SEQ ID NO 6
<211> LENGTH: 27
<212> TYPE: DNA
<213> ORGANISM: Synthetic DNA

<400> SEQUENCE: 6
cggtcgacag gcaggcatgc aagctta                                    27

<210> SEQ ID NO 7
<211> LENGTH: 28
<212> TYPE: DNA
<213> ORGANISM: Synthetic DNA

<400> SEQUENCE: 7
cgctcgagtt taggattgta agctgtgc                                   28
```